United States Patent [19]

Makabe et al.

[11] Patent Number: 4,482,245
[45] Date of Patent: Nov. 13, 1984

[54] APPARATUS FOR MEASURING THE COLOR OF A BRILLIANT-CUT DIAMOND

[75] Inventors: Hideki Makabe, Muko; Toyoji Yamamoto, Tokorozawa; Yoshio Matsueda, Iida; Yasunori Ito, Iida; Katsuto Yamada, Iida, all of Japan

[73] Assignee: Kalnew Optical Industrial Co., Ltd., Japan

[21] Appl. No.: 444,606

[22] Filed: Nov. 26, 1982

[30] Foreign Application Priority Data

Nov. 30, 1981 [JP] Japan .................... 56-193413

[51] Int. Cl.³ .................................. G01J 3/46
[52] U.S. Cl. .......................... 356/30; 356/244
[58] Field of Search ............... 356/30, 236, 244

[56] References Cited

FOREIGN PATENT DOCUMENTS 2036360 6/1980 United Kingdom .................. 356/30

Primary Examiner—F. L. Evans
Attorney, Agent, or Firm—Hubbell, Cohen, Stiefel & Gross

[57] ABSTRACT

An apparatus for measuring a diamond color comprises a light source composed of a lamp and an integrating sphere for diffusing light therein emitted from the lamp; a diamond holder including diamond supporting head means and suction base means, thereby positioning the table facet of the diamond in the integrating sphere for allowing the diffused light from the light source to fall on the table facet of the diamond; a monochromator for separating a beam of light as it emerges from the diamond through the table facet side into a spectrum; a photodetector for detecting the light from the monochromator; variable slit means disposed in at least one of the monochromator and the photodetector for adjusting the size of the beam of light to a diameter of the diamond; a measurement unit for controlling at least the monochromator to obtain a spectrum of the light which has passed through the diamond; and an arithmetic unit for deriving tristimulus values X, Y and Z from the spectrum of the light from the diamond; which is able to measure the colors of brilliant-cut diamonds easily and objectively.

4 Claims, 6 Drawing Figures

APPARATUS FOR MEASURING THE COLOR OF A BRILLIANT-CUT DIAMOND

BACKGROUND OF THE INVENTION

1. Field of the Invention

The present invention relates to an apparatus for measuring the color of a brilliant-cut diamond, and more particularly to such an apparatus for measuring the spectrum of a beam of light that has passed through a diamond, deriving tristimulus values X, Y and Z from the measured spectrum, and evaluating the color grade of the diamond.

2. Description of the Prior Art

Diamonds are normally evaluated by the qualities of "Four C's": color, clarity, cutting and carat weight. Color determination has heretofore been conducted by an organoleptic examination in which the hue of yellow is classified by human eyes into grades ranging from water-whiteness to light yellow for evaluation.

The organoleptic color determination however lacks objectivity no matter how skilled the observer may be. It frequently occurs in reality that a diamond color is differently judged by different observers. Proper determination of diamond colors is more desired since diamonds are getting more and more popular among people and their market is expanding. There has been a need for apparatus for properly measuring diamond colors without resorting to subjectified judgement by human observers.

SUMMARY OF THE INVENTION

It is an object of the present invention to provide an apparatus for effectively determining the color of a brilliant-cut diamond objectively.

According to the present invention, there is provided an apparatus for measuring a diamond color, comprising a light source composed of a lamp and an integrating sphere for diffusing light therein emitted from the lamp; a diamond holder including diamond supporting head means having in an upper portion thereof a pavilion hole for receiving the pavilion of a brilliant diamond to be measured and a suction aperture extending from the pavilion hole to a lower portion thereof, and suction base means having on an upper portion thereof a tapered portion removably fitted in the diamond supporting head means for holding the diamond received in the pavilion hole under suction developed in the suction aperture, thereby positioning the table facet of the diamond in the integrating sphere for allowing the diffused light from the light source to fall on the table facet of the diamond; a monochromator for separating a beam of light as it emerges from the diamond through the table facet side into a spectrum; a photodetector for detecting the light from the monochromator; variable slit means disposed in at least one of the monochromator and the photodetector for adjusting the size of the beam of light to a diameter of the diamond; a measurement unit for controlling the monochromator to obtain a spectrum of the light which has passed through the diamond; and an arithmetic unit for deriving tristimulus values X, Y and Z from the spectrum of the light from the diamond.

The apparatus for measuring diamond colors according to the present invention is of great practical advantage in that it can objectively measure the colors of brilliant-cut diamonds, and can produce measured outputs which can easily be converted to color grades of the type which has widely been used conventionally.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
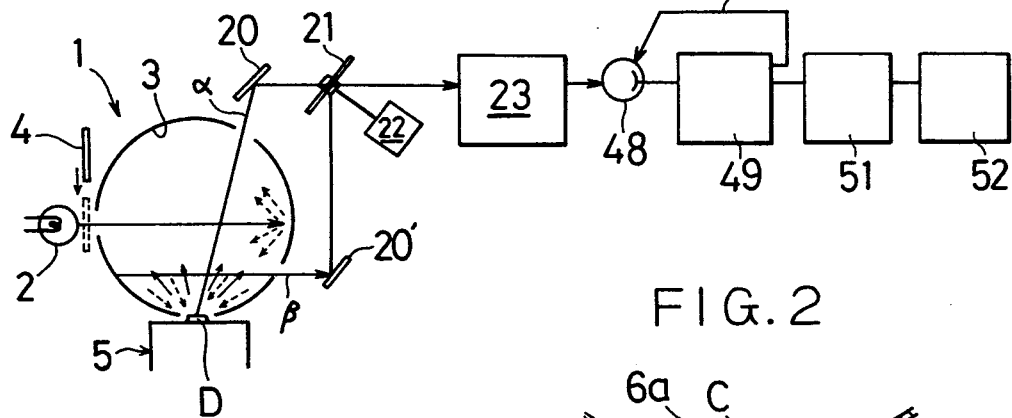
FIG. 1 is a schematic view, partly in block form, of an apparatus for measuring diamond colors according to an embodiment of the present invention.

FIG. 1 shows an apparatus, generally indicated at 1, for measuring the color of a billiant-cut diamond according to the present invention.

The apparatus 1 has a light source basically comprising a halogen lamp 2 and an integrating sphere 3 for producing diffused light through multiple reflection by an inner surface thereof of white light emitted from the halogen lamp 2. The light source also includes an ultraviolet radiation cut-off filter 4 when any influence by fluorescence of a diamond being measured shall be removed.

Figure 2:
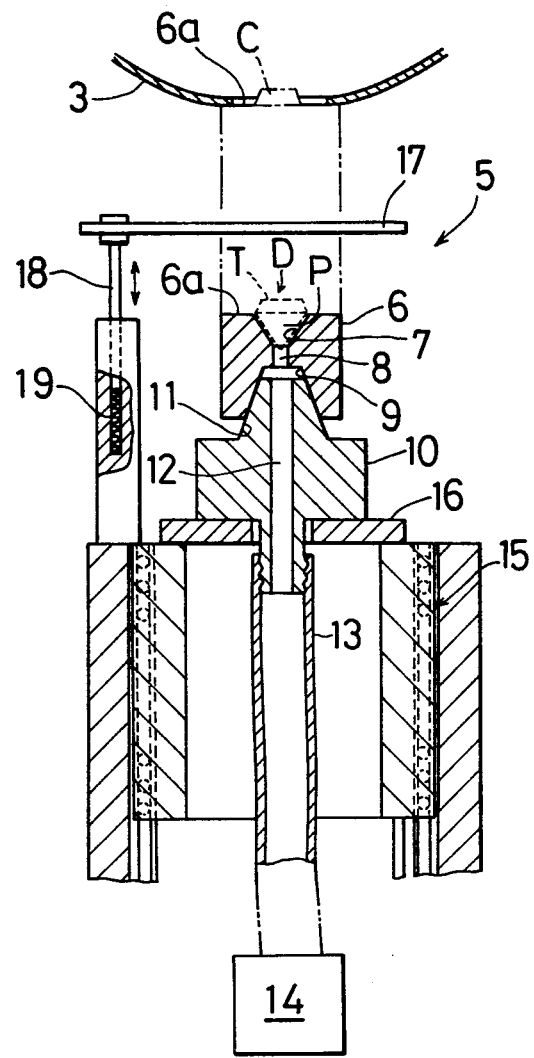
FIG. 2 is an enlarged fragmentary cross-sectional view of a diamond holder in the apparatus shown in FIG. 1.

As shown in FIG. 2, a holder 5 for supporting a brilliant-cut diamond D is basically composed of a diamond supporting head 6 and a suction base 10, and desirably it includes a table setting plate 17 for causing a table T of the diamond D to lie at a predetermined angle of inclination. The diamond supporting head 6 is made of ceramics of standard white and has in its upper surface a pavilion hole 7 for complementarily receiving a pavilion P of the diamond D and in its lower surface a recess 9 in the shape of a truncated cone, the pavilion hole 7 and the recess 9 being held in communication with each other through a suction aperture 8.

The suction base 10 has on its upper surface a projection 11 shaped as a truncated cone and closely fitted in the recess 9 and a through hole 12 extending from an upper surface of the projection 11 all the way down to a bottom of the suction base 10. The through hole 12 is connected by a joint pipe 13 to a suction pump 14.

The projection 11 of the suction base 10 and the recess 9 in the diamond supporting head 6 have precision tapered surfaces such that the projection 11 is fitted intimately in the recess 9 in coaxial relationship. The diamond supporting head 6 is simply placed on the suction base 10 for easy detachment therefrom.

The apparatus 1 according to the present invention has a plurality of such diamond supporting heads 6 selectively available with their pavilion holes 7 sized to diamonds D of various dimensions. In operation, one of the diamond supporting heads 6 is selected which has the pavilion hole 7 conforming to the size of a diamond D to be measured, and is mounted on the suction base 10. The capability for the available diamond supporting heads 6 to be easily attached to or detached from the suction base 10 allows optimum diamond supporting heads 6 to be readily mounted in position on the suction base 10 for varying sizes of diamonds D to be measured.

The suction base 10 is affixed to a stage 16 movable upwardly and downwardly by a lifter mechanism 15. When the diamond D or the diamond supporting head 6 is to be exchanged with another, the suction base 10 is lowered. The suction base 10 is raised for measuring the diamond D installed on the diamond supporting head 6. When the suction base 10 is in the raised position, the diamond supporting head 6 has an upper surface 6a held against an outer peripheral surface of the integrating sphere 3 with a crown C of the diamond D being positioned within the integrating sphere 3, as illustrated by the imaginary lines in FIG. 2. The lifter mechanism 15 comprises a steel-ball sliding mechanism for keeping the stage 16 in exact axial alignment when it moves upwardly and downwardly.

The table setting plate 17 is supported on and rotatable about a shaft 38 which is movable vertically against the resiliency of a spring 19.

For mounting a diamond D to be measured on the diamond supporting head 6, the latter is first installed on the suction base 10 when the stage 16 is in the lowered position. The diamond D is then fitted in the pavilion hole 7 in the diamond supporting head 6. The table setting plate 17 is pressed down against the table T of the diamond D thus mounted to cause the table T to be inclined at a predetermined angle, and at the same time the suction pump 14 is actuated to hold the diamond D under suction on the diamond supporting head 6. Finally, the table setting plate 17 is turned about the shaft 18 out of a vertical path of movement of the diamond supporting head 6, and the stage 16 is raised up by the lifter mechanism 15.

As illustrated in FIG. 1, diffused light falling on the table facet side of the diamond D enters the latter, undergoes multiple reflection therein, and emerges from the table facet side of the diamond D as a beam of light $\alpha$. The beam of light $\alpha$ travels substantially perpendicularly to the table T of the diamond D and comes out of the integrating sphere 3 and is guided by a mirror 20 and a chopping mirror 21 to a monochromator 23. A beam of light $\beta$ serving as a reference light in a double-beam system is picked up from a portion of the integrating sphere 3 and guided by a mirror 20' and the chopping mirror 21. The chopping mirror 21 is rotatable by a motor 22 so that the beams of light $\alpha,\beta$ will alternately be directed to the monochromator 23.

Figure 3:
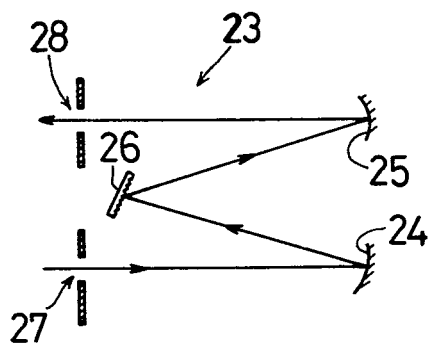
FIG. 3 is a schematic view of a spectroscope in the apparatus of FIG. 1.

As illustrated in FIG. 3, the monochromator 23 comprises two mirrors 24, 25, a single grating 26, and a pair of variable slits 27, 28 serving as a light inlet and a light outlet, respectively.

Figure 4:
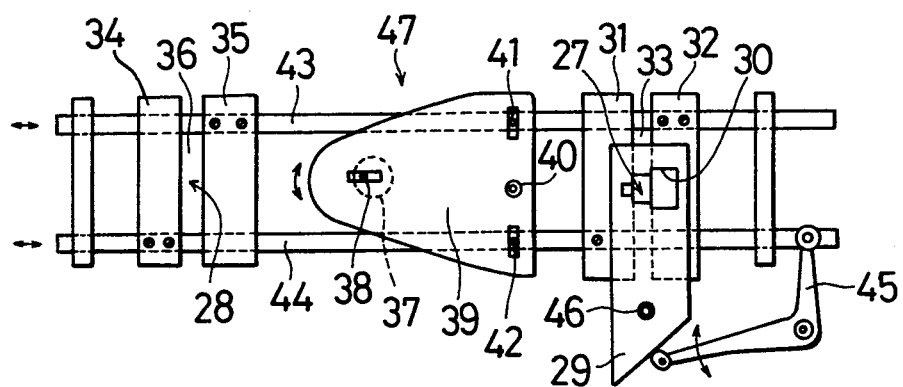
FIG. 4 is an enlarged front elevational view of a variable slit mechanism in the spectroscope illustrated in FIG. 3.

FIG. 4 shows a construction of such variable slits 27, 28. The inlet slit 27 is defined by a window 30 in a switching mask plate 29 and a gap 33 between two slit blades 31, 32, and the outlet slit 28 is defined by a gap 36 between two slit blades 34, 35. The sizes of these slits 27, 28 will be changed as follows: When a shaft 37 is turned by a pulse motor (not shown), a pin 38 mounted eccentrically on the shaft 37 causes a cam plate 39 to be angularly moved about a pin 40. Pins 41, 42 mounted on bars 43, 44 and held loosely in engagement with the cam plate 39 are then moved in opposite directions, enabling the bars 43, 44 to move in opposite directions. The slit blades 32, 35, and 31, 34 which are attached to the bars 43, 44, respectively, are moved apart from or toward each other to vary the gaps 33, 36 which define the slits 27, 28, respectively. When the bar 44 moves, a switching lever 45 causes the switching mask plate 29 to angularly move about a pin 46 thereby displacing the window 30 with respect to the gap 33. The window 30 is shaped such that it will provide different sizes which change stepwise or continuously with respect to the gap 33. As the switching mask plate 29 is thus moved, therefore, the size of the slit 27 varies. The slit 27 should preferably be of a size inscribed in a circle having the same diameter as that of the diamond D being measured.

As shown in FIG. 1, the beam of light as it emerges from the monochromator 23 enters a photomultiplier 48 in which the beam of light is converted into an electric signal proportional to the intensity of the light.

A measurement unit 49 serves to control the spectral wavelengths in the monochromator 23 for producing a spectrum of the light from the diamond D in the range of from about 380 to 780 nm and additionally can serve to generate a feedback signal 50 based on the reference light detected in synchronism with the chopping mirror 21 for changing a negative voltage applied to the photomultiplier 48 for automatic adjustment of the sensitivity thereof.

An arithmetic unit 51 serves to derive tristimulus values X, Y and Z from the spectrum produced by the measurement unit 49 based on the following arithmetic operations:

$$X = K \int \psi(\lambda) \bar{x}(\lambda) d\lambda \qquad (I)$$

$$Y = K \int \psi(\lambda) \bar{y}(\lambda) d\lambda \qquad (II)$$

$$Z = K \int \psi(\lambda) \bar{z}(\lambda) d\lambda \qquad (III)$$

where $\psi(\lambda)$ is the spectrum, $\bar{x}(\lambda)$, $\bar{y}(\lambda)$ and e,ovs/z/ $(\lambda)$ are the color matching functions, and K is a constant for equalizing Y to the amount of the measured light. These values X, Y and Z are delivered to a printer plotter 52.

The tristimulus values X, Y and Z obtained by the arithmetic unit 51 are compared with a color grade table which shows the known estimated color grades of diamonds, so that the color grade of the diamond D can objectively be determined. For easier determination of the color grade, the arithmetic unit 51 effects the following arithmetic operations to derive chromaticity coordinates x and y from the tristimulus values X, Y and Z:

$$x = X/(X+Y+Z) \qquad (IV)$$

$$y = Y/(X+Y+Z) \qquad (V)$$

Figure 5:
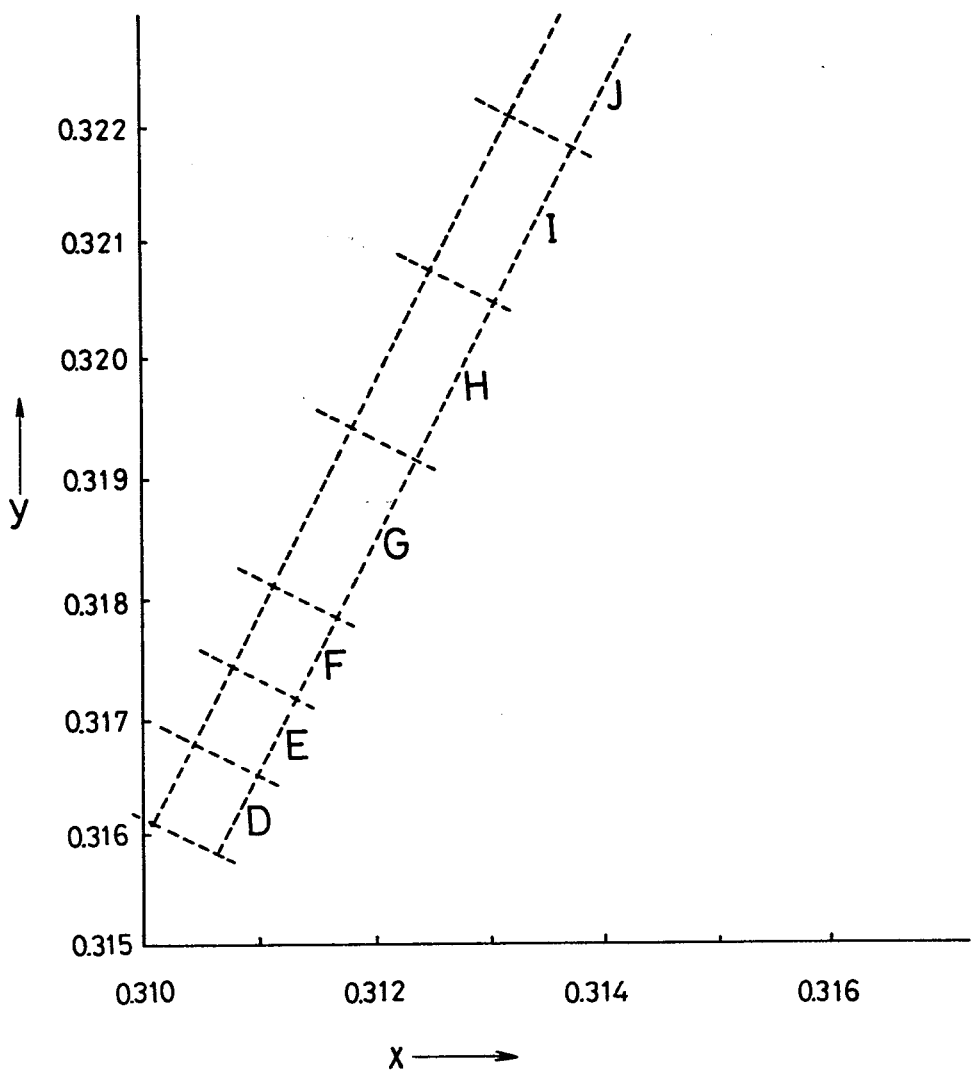
FIG. 5 is a view showing a chart sheet used in the apparatus of FIG. 1.

Then the chromaticity coordinates x and y are supplied as inputs to the printer plotter 52 to put down a coordinate point on a chart sheet as shown in FIG. 5 which is set in the printer plotter 52.

Figure 6:
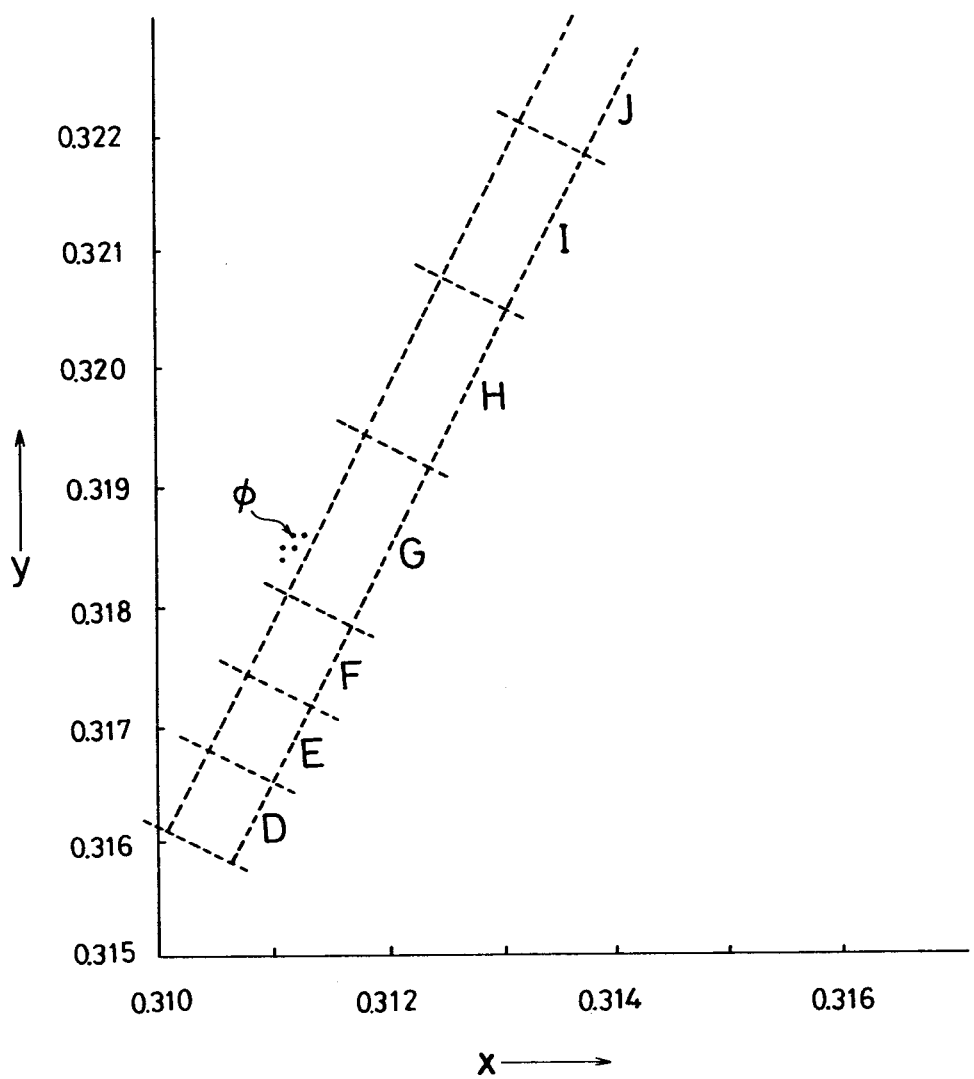
FIG. 6 is a view of a chart prepared by the apparatus shown in FIG. 1.

The operator can now have a chart as illustrated in FIG. 6. The coordinate point ($\phi$) in the example shown in located in an area "G". Thus, the operator knows that the color grade of the diamond D is a grade "G".

The chart sheet shown in FIG. 5 is prepared by measuring a number of diamonds on the apparatus 1 which have known color grades determined by the system of G.I.A. (Gemological Institute of America), plotting a number of coordinate points thus obtained on a chromaticity diagram, thereby empirically preparing a scale (as shown by the dotted lines), and drawing such a scale on a coordinate system (as shown by the solid lines) which has been picked up from the chromaticity diagram. Therefore, the color grades are determined by the G.I.A. system.

Other color grade determination includes that which is carried out by the system of C.I.B.J.O. (International Confederation of Jewelry, Silverware, Diamonds, Pearls and Stones). With this system, a scale can be prepared in the manner described above, and such a scale is graduated on a transparent plate to thereby make a template. The color grade of the diamond can easily be determined in the other system by placing such a template on the diagram of FIG. 6.

As described above, the apparatus according to the present invention can objectively measure the colors of brilliant-cut diamonds. Since outputs of the apparatus can easily be converted into conventional color grade values which have widely been used heretofore, the apparatus is highly advantagous in practical use. The holder and the diameter of a beam of light can be changed to suit the size of a diamond to be measured, so that the girdle portion of the diamond can be located in the same position with respect to the integrating sphere at all times and only the crown portion of the diamond can be irradiated with light. The light from the diamond can be received in an appropriate amount for color measurement with high accuracy.

Although a certain preferred embodiment has been shown and described, it should be understood that many changes and modifications may be made therein without departing from the scope of the appended claims.

What is claimed is:

1. An apparatus for measuring a diamond color, comprising:
   (a) a light source composed of a lamp and an integrating sphere for diffusing light therein emitted from said lamp;
   (b) a diamond holder comprising (i) diamond supporting head means having in an upper portion thereof a pavilion hole for receiving the pavilion of a brilliant-cut diamond to be measured and a suction aperture extending from said pavilion hole to a lower portion thereof, and (ii) suction base means having on an upper portion thereof a tapered portion removably fitted in said diamond supporting head means for holding the diamond received in said pavilion hole under suction developed in said suction aperture, thereby positioning the table facet of the diamond in said integrating sphere for allowing the diffused light from the light source to fall on the table facet of the diamond;
   (c) a monochromator for separating a beam of light as it emerges from the diamond through the table facet side into a spectrum;
   (d) a photodetector for detecting the light from said monochromator;
   (e) variable slit means disposed in at least one of said monochromator and said photodetector for adjusting the size of the beam of light to a diameter of the diamond;
   (f) a measurement unit for controlling at least said monochromator to obtain a spectrum of the light which has passed through the diamond; and
   (g) an arithmetic unit for deriving tristimulus values X, Y and Z from said spectrum of the light from the diamond.

2. An apparatus according to claim 1, wherein said diamond holder further comprises a table setting means for setting the table facet of the diamond mounted in said pavilion hole at a predetermined angle of inclination.

3. An apparatus according to claim 1, including a plurality of diamond supporting head means having respectively pavilion holes shaped differently to suit diamonds of various sizes, said diamond supporting head means being selectively mounted on said suction base means to meet the size of the diamond to be measured.

4. An apparatus according to claim 2, including a plurality of diamond supporting head means having respectively pavilion holes shaped differently to suit diamonds of various sizes, said diamond supporting head means being selectively mounted on said suction base means to meet the size of the diamond to be measured.

* * * * *